(12) United States Patent
Diebold et al.

(10) Patent No.: US 7,865,242 B2
(45) Date of Patent: Jan. 4, 2011

(54) PATIENT DEVICE

(75) Inventors: Michael Diebold, Berlin (DE); Eric Fournie, Erlangen (DE); Jim Horton, Portland, OR (US); Julian Merlin, Berlin (DE); Jens Potschadtke, Erlangen (DE); Andre Seidelt, Berlin (DE); Paul Stadnik, Lake Oswego, OR (US); Sven Bode, Berlin (DE); Jim Nelson, Lake Oswego, OR (US)

(73) Assignee: Biotronik CRM Patent AG, Baar (CH)

( * ) Notice: Subject to any disclaimer, the term of this patent is extended or adjusted under 35 U.S.C. 154(b) by 1389 days.

(21) Appl. No.: 11/332,947

(22) Filed: Jan. 17, 2006

(65) Prior Publication Data

US 2006/0159074 A1      Jul. 20, 2006

(30) Foreign Application Priority Data

Jan. 18, 2005     (EP)     ................................ 05075125

(51) Int. Cl.
*A61N 1/00* (2006.01)
(52) U.S. Cl. ........................................................ 607/32
(58) Field of Classification Search ................ 607/32, 607/60, 30; 128/903, 904; 379/37–38, 40, 379/45, 106.01, 106.02; 455/456.1, 562.1
See application file for complete search history.

(56) References Cited

U.S. PATENT DOCUMENTS

| | | | | | |
|---|---|---|---|---|---|
| 4,689,811 | A | * | 8/1987 | Lennstrom et al. | 379/38 |
| 5,752,976 | A | * | 5/1998 | Duffin et al. | 607/32 |
| 5,754,111 | A | * | 5/1998 | Garcia | 340/573.1 |
| 5,933,080 | A | * | 8/1999 | Nojima | 340/426.19 |
| 6,131,136 | A | * | 10/2000 | Liebenow et al. | 710/316 |
| 6,470,215 | B1 | * | 10/2002 | Kraus et al. | 607/60 |
| 6,553,262 | B1 | * | 4/2003 | Lang et al. | 607/32 |
| 6,564,104 | B2 | * | 5/2003 | Nelson et al. | 607/60 |
| 6,574,509 | B1 | * | 6/2003 | Kraus et al. | 607/60 |
| 6,657,989 | B1 | * | 12/2003 | Hilsenrath | 370/351 |

(Continued)

FOREIGN PATENT DOCUMENTS

EP          0 695 075 A1     1/1996

(Continued)

*Primary Examiner*—Mark W Bockelman
*Assistant Examiner*—Roland Dinga
(74) *Attorney, Agent, or Firm*—Hahn Loeser & Parks, LLP; John J. Cunniff

(57) ABSTRACT

The invention relates to a patient's device having an at least unidirectional, wireless interface for receiving a data signal. The wireless interface is adapted to receive medical or operational data from a medical device, in particular an implantable medical device like a cardiac pacemaker or a cardioverter/defibrillator, a data communication interface for accessing a wide area network or a public telecommunication network or both. The device comprises an automatic routing/dialling module connected to the data communication interface, adapted to establish an automatic access to a modem connected to the data communication interface by automatically selecting one of a plurality of possible connection parameters. The connection parameters are selected from at least one of an individual modem, if more than one modem is connected to the data communication interface, and a prefix number for a remote access to a remote device over a public network automatically selecting a dial-up telephone number.

20 Claims, 1 Drawing Sheet

U.S. PATENT DOCUMENTS

| | | | |
|---|---|---|---|
| 6,671,351 B2 * | 12/2003 | Menard et al. | 379/45 |
| 6,807,268 B1 * | 10/2004 | Wierzbitzki et al. | 379/211.01 |
| 2001/0029321 A1 * | 10/2001 | Beetz et al. | 600/300 |
| 2002/0045804 A1 * | 4/2002 | Christopherson et al. | 600/300 |
| 2003/0062989 A1 * | 4/2003 | Tsunezumi | 340/286.07 |
| 2003/0139778 A1 | 7/2003 | Fischell et al. | |
| 2004/0059205 A1 * | 3/2004 | Carlson et al. | 600/310 |

FOREIGN PATENT DOCUMENTS

| | | |
|---|---|---|
| WO | WO 00/16540 A1 | 3/2000 |

* cited by examiner

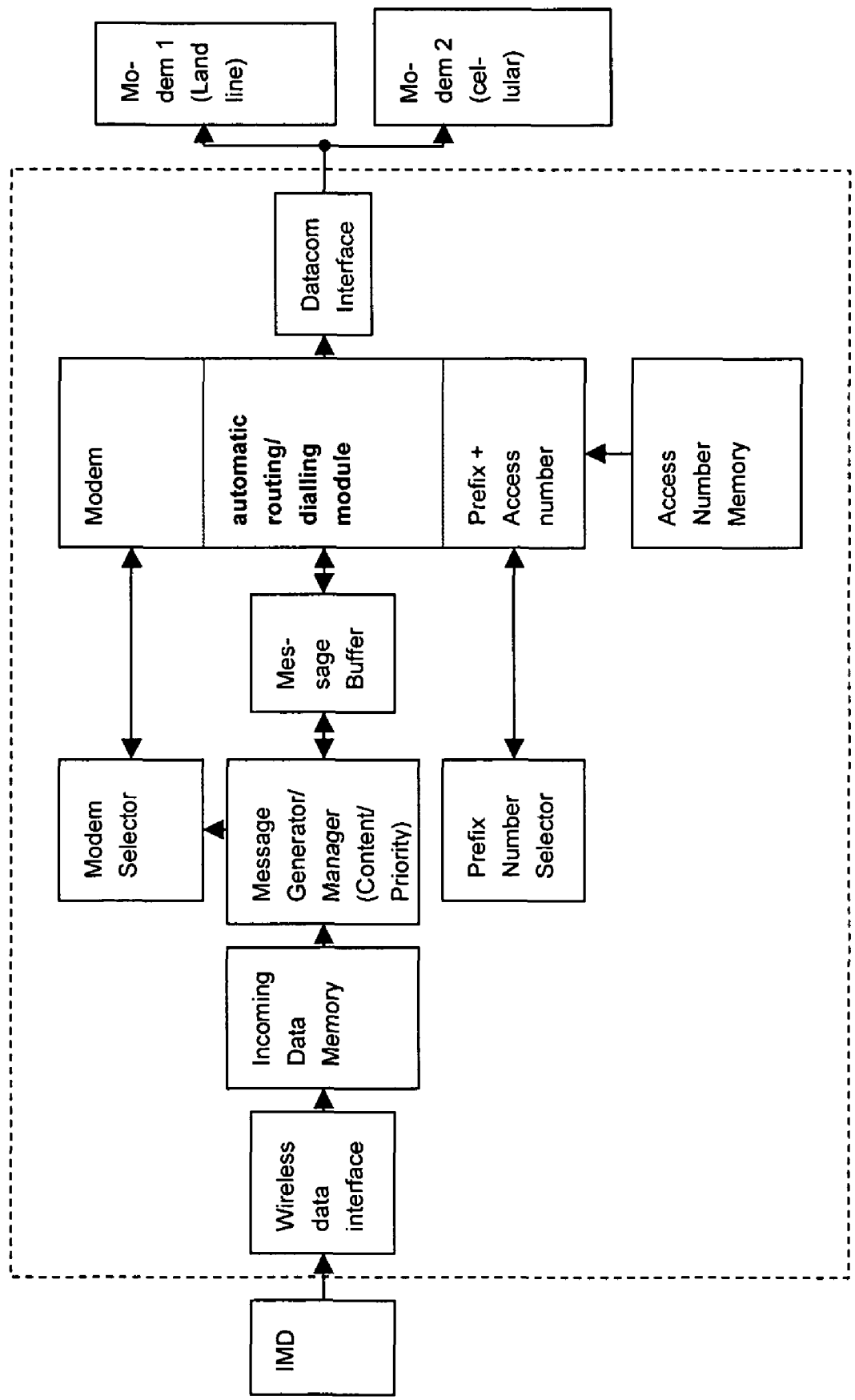

PATIENT DEVICE

CROSS REFERENCE TO RELATED APPLICATIONS

This application claims priority from European Application No. 05 075 125.4, filed on Jan. 18, 2005, which is incorporated by reference herein.

BACKGROUND OF THE INVENTION

The invention relates to a patient device having an at least unidirectional, wireless interface for receiving a data signal from a medical device, in particular an implantable medical device (IMD) such as a cardiac pacemaker or an implantable cardioverter/defibrillator (ICD) or the like. The patient device further comprises a data communication interface for accessing a wide area network (WAN) or a public telecommunication network or both.

Such a patient device is also known as a bedside device and is usually placed in the proximity of a patient wearing an implantable cardiac pacemaker or an implantable cardioverter/defibrillator. The patient device usually is able to receive medical or operational data from the medical device via the wireless interface. Common patient devices further comprise a data communication interface enabling the patient device to pass on data received from the implanted medical device to a central server operated by a central service center, also known as home-monitoring service center.

The data communication interface usually is connected to a modem. In order to access a remote device like a central server via a public telephone network, a telephone number has to be dialled by the modem. The number to be dialled depends on the location and the environment the modem is used in. Therefore, it may be difficult for a user to set up the patient device in a correct manner so that it works in a particular environment.

Furthermore, the patient device may be connected to more than one modem, for example, to both a landline modem and a cellular modem. In such case, the user has to choose one of the available access technologies (for example landline modem or cellular modem) prior to establishing a remote access. The patient is not always aware of whether a particular access technology is available for the moment being because, for example the landline may be engaged or the cellular phone temporarily has no access to the cellular network.

The problems mentioned not only cause some inconvenience for the patient, they also bear the risk that an important message from the implantable medical device is not transmitted to the central service center in time.

This problem so far has not been addressed in the art.

BRIEF SUMMARY OF THE INVENTION

In order to solve this problem according to the invention, it is suggested to equip a patient device as introduced here before with an automatic routing/dialling module connected to the data communication interface and being adapted to establish an automatic access to a modem connected to the data communication interface by automatically selecting one of a plurality of possible connection parameters, the connection parameters to be selected include an individual modem, if more that one modem is connected to the data communication interface, or a prefix number for remote access to remote access device over a public network, or both.

The invention is based on the insight that oftentimes in addition to an access number, for example a dial-up or telephone number, a prefix number is necessary to access a public line via a private branch exchange environment or if the central server is placed out of country. The prefix number may include the prefix the private branch exchange requires to access a public line. The prefix number additionally may be a country code or an area code to be dialled prior to an individual access number that individual access number, generally being a dial-up telephone number. There may be other access numbers for sending out an SMS via a cellular phone network.

Typical modems a patient device may be connected to and to be selected from prior to establishing a remote access may include a landline modem and a cellular modem. In general, the data communication interface may as well be connected to other known access technologies.

In a preferred embodiment, the automatic routing/dialling module comprises or is connected to an access number memory containing an access number to be dialed for establishing a data communication to a dedicated remote device such as a central server. The access number usually will be a dial-up telephone number. The access number can be stored in the access number memory by a service provider prior to delivery of the patient device to the patient. In such case, the patient does not have to store or program any access number into the patient device.

Furthermore, the automatic routing/dialling module preferably comprises or is connected to a prefix number selector comprising or being connected to a prefix number memory, which contains a prefix number list. The prefix number list contains a prefix number or a plurality of prefix numbers to be dialled prior to the access number in order to establish a remote data access to a remote device. The prefix number selector is adapted to select one of the prefix numbers from the prefix number list any time a remote access shall be established. Preferably, the prefix number selector is adapted to select the prefix number according to a programmable prefix number selection rule base. In particular, the prefix number selector may be adapted to first select a first prefix number from the prefix number list and to receive a connection-not-established-signal from the automatic routing/dialling module if that first prefix number has not led to a successful data communication and, upon receiving the connection-not-establish-signal to select a second prefix number from the prefix number list for a second attempt to establish a remote access. Reselection of a prefix number is repeated until the prefix number selector does not receive a connection-not-established-signal from the automatic routing/dialling module or if all prefix numbers from the list have already been tried. In the latter case, the prefix number selector preferably is adapted to output a warning or alarm signal.

In a preferred embodiment of the prefix number selector, the prefix number selector is adapted to always choose the prefix number having the first place in the prefix number list first. In such case, the prefix number selectors preferably is adapted to move that prefix number leading to a successful remote access (when no connection-not-established-signal is received) to the first place in the prefix number list. Thus, the prefix number selector is able to automatically adapt to changes in the environment, for example if the patient has moved to another location or if one of the modems is hooked up to a different private branch exchange or if the private branch exchange has been changed.

The great advantage of such prefix number selector is that the patient does not have to care for choosing a correct prefix number unless a warning or alarm signal is generated by the prefix number selector and is indicated by the patient device.

In a further preferred embodiment, the prefix number selection rule base may be reprogrammable to perform a prefix number selection rule base update if available.

In addition to a prefix number selector or instead of a prefix number selector, the automatic routing/dialling module may comprise a modem selector. Said modem selector is adapted to receive a modem-type signal from the automatic routing/dialling module for each available modem connected to the data communication interface. The modem selector furthermore is adapted to select one modem from the available modems according to a modem selection rule base. The modem selection rule base may be programmable in a preferred embodiment.

Preferably the modem selector is adapted to choose one available modem according to the following rules:
   a) choose a landline modem if a landline network is accessible, but a cellular network is not,
   b) choose a cellular modem if a cellular network is accessible, but a landline network is not,
   c) choose a landline modem if both, a landline modem having access to a landline network and a cellular modem having access to a cellular network, are available, but a landline connection entails lower cost,
   d) keep a message in a message buffer memory for later transmission if no accessible modem is available,
   e) keep a low priority message in a message buffer memory for later transmission if only a cellular modem is accessible
   f) choose a cellular modem if both, a landline modem having access to a landline network and a cellular modem having access to a cellular network are available, but a landline connection is engaged,
   g) choose a landline modem for messages exceeding a predetermined length or data amount.

Preferably, the automatic routing/dialling module is adapted to initiate a remote communication connection via an available modem connected to the data communication interface depending on both, on the type of available modem and the priority of a message to be communicated or transmitted. This allows to select any available modem for high priority messages. Low priority messages can be stored in the message buffer memory for later transmission when a cheaper access technology is available.

To compose messages to be transmitted from the data received from the implantable medical device and to assign a priority indicator to each message, a message generator/manager is provided in a preferred embodiment which is at least indirectly connected to the wireless interface to receive medical or operational data from the implantable medical device and which is adapted to submit the message to be transmitted together with the assigned priority indicator to the automatic routing/dialling module. In such embodiment, the modem selector is preferably connected to the message generator/manager to enable the modem selector to choose a modem based upon the priority indicator assigned a message to be transmitted.

Furthermore, a data buffer memory may be provided which is at least indirectly connected to the automatic routing/dialling module and which serves for storing a message until its successful transmission. Also, an incoming data memory which is at least indirectly connected to the wireless interface for storing the medical or operational data received via the wireless interface may be provided. The data buffer memory and the incoming data memory may be parts of a common memory forming a shared memory.

In a preferred patient device, the message generator/manager is adapted to read data from the incoming data memory and to write message data and assigned priority indicator data into the data buffer memory.

The message generator/manager may be adapted to assign a timestamp to each message indicating the time when the message has been created. If transmission of a low priority message is delayed by a predetermined period of time, the message generator/manager can increase the priority of the message in order to avoid an indefinite delay if for example a landline connection is not available for a longer period of time.

BRIEF DESCRIPTION OF THE DRAWING

The invention shall now be disclosed by way of an example shown in FIG. 1.

In FIG. 1, a patient device is indicated by a rectangular block framed by a dashed line.

DETAILED DESCRIPTION OF THE INVENTION

The components of the patient device shown in FIG. 1 are: a wireless data interface, an incoming data memory, a message generator/manager, a message buffer memory, a modem selector, a prefix number selector, an automatic routing/dialling module, an access number memory and a datacom interface.

Of course, the patient device may comprise further components such as a warning indicator or a keyboard interface enabling the manual input of data. Furthermore, the patient device comprises a power supply. These components are not shown as they are known in the art.

In operation, the wireless data interface is connected wirelessly to an implantable medical device (IMD). The wireless data interface is also connected to the incoming data memory to write data received from the IMD into the incoming data memory. The message generator/manager has access to the data memory and is adapted to form a message from the data saved in the incoming data memory. The data in the incoming data memory may be medical or operational data indicating a patient's health state or an operational state of the implantable medical device, respectively.

Furthermore, the message generator/manager is adapted to create a priority indicator for each message depending on the urgency the data from the incoming data memory needs to be transmitted to a central service center.

If a message is ready for transmission, the message generator/manager writes the message into the message buffer memory and triggers the automatic routing/dialling module.

The automatic routing/dialling module is adapted to read out the message buffer memory and to establish a data communication to a remote device like a central server by initiating a remote access. The remote access may be initiated instantaneously by the automatic routing/dialling module if the message to be transmitted bears a high priority. Otherwise, the automatic routing/dialling module may be adapted to send low priority messages based on a time schedule. Thus, the automatic routing/dialling module may be connected to a timer, which is not shown.

If the automatic routing/dialling module is about to initiate remote access, the automatic routing/dialling module needs to select a modem if more than one modem is available. Furthermore, the automatic routing/dialling module will access the access number memory containing the access number to access the remote device. Since the access number alone may not be sufficient to establish a data communication, an additional prefix number to be dialled prior to the access number may be necessary. Selection of an appropriate prefix number is carried out by the prefix number selector.

The prefix number selector has access to a prefix number list and is adapted to choose the first prefix number from the list for an initial attempt to set up a data communication. If the first prefix number from the list does not lead to a successful data communication, the automatic routing/dialling module will generate a communication-not-established-signal which causes the prefix number selector to select the second number from the list for a second data transmission attempt. This selection of a prefix number is repeated until a successful data transmission is established.

For selecting one of the available modems, the automatic routing/dialling module is connected to a modem selector which may be an integral part of the automatic routing/dialling module. The modem selector automatically administrates the list of all available modems. The list of modems comprises the modem type and may contain further data like data relating to transmission costs and to transmission speed (baud rate).

The modem selector is adapted to choose among the available modems the modem providing the best transmission performance and the lowest transmission costs. That will generally be a landline modem. If the preferred modem is not accessible, e.g. the landline is occupied, the modem selector will select an alternative modem, for example a cellular modem.

Selection of a modem may also depend on the priority of the message to be transmitted. If an individual modem is selected and the first prefix number is determined together with the access number, the automatic routing/dialling module accesses the datacom interface based on the modem/prefix number/access number data in order to attempt to establish a data communication leading to a remote access to a central server. If that attempt should fail, the attempt will be repeated using a next prefix number.

Should all possible attempts to establish a data communication fail, the automatic routing/dialling module will generate a warning or an alarm signal to indicate the patient that no successful data communication could be established.

What is claimed is:

1. A patient's device having
an at least unidirectional, wireless interface for receiving a data signal, the wireless interface being adapted to receive medical or operational data from an implantable medical device,
a data communication interface for accessing a wide area network or a public telecommunication network or both
wherein the patient's device further comprises an automatic routing/dialling module connected to the data communication interface and being adapted to establish an automatic access to a modem connected to the data communication interface
by automatically selecting one of a plurality of possible connection parameters, the connection parameters to be selected including at least one of
an individual modem, if more than one modem is connected to the data communication interface, and
a prefix number for a remote access to a remote device over a public network
automatically selecting a dial-up telephone number,
wherein the automatic routing/dialling module is adapted to initiate a remote data communication connection via an available modem connected to the data communication interface depending both on the type of available modem and the priority of a message to be communicated,
wherein the automatic routing/dialling module comprises or is connected to an access number memory containing an access number for establishing a data communication to a remote device, and
wherein the automatic routing/dialling module comprises or is connected to a prefix number selector comprising or being connected to a prefix number memory containing a prefix number list, wherein the prefix number list contains prefix numbers to be dialled prior to the access number.

2. A patient's device according to claim 1, wherein the prefix number selector is adapted to select a prefix number according to a programmable prefix number selection rule base.

3. A patient's device according to claim 1, wherein the prefix number selector is adapted to always select a first prefix number in the prefix number list and to receive a connection-not-established-signal from the automatic routing/dialling module if the prefix number has not led to a successful data communication and, upon receiving the connection-not-established-signal, select the second prefix number from the prefix number list and to repeat a prefix number selection upon receiving a connection-not-established-signal until the last prefix number from the prefix list is reached.

4. A patient's device according to claim 3, wherein the prefix number selector is adapted to generate an error signal if selection of the last prefix number from the prefix number list has led to a connection-not-established-signal.

5. A patient's device according to claim 3, wherein the prefix number selector is adapted to automatically modify the prefix number list by moving the first prefix number not leading to a connection-not-established-signal to the first place in the prefix number list.

6. A patient's device according to claim 1, wherein the automatic routing/dialling module comprises a modem selector, said modem selector receiving a modem-type signal from the automatic routing/dialling module for each available modem connected to the data communication interface and being adapted to select one modem from the available modems according to a modem selection rule base.

7. A patient's device according to claim 6, wherein the modem selection rule base is programmable.

8. A patient's device according to claim 6, wherein the modem selector is adapted to choose one available modem according to the following rules:
a) choose a landline modem if a landline network is accessible, but a cellular network is not,
b) choose a cellular modem if a cellular network is accessible, but a landline network is not,
c) choose a landline modem if both, a landline modem having access to a landline network and a cellular modem having access to a cellular network, are available, but a landline connection entails lower cost,
d) keep a message in a message buffer memory for later transmission if no accessible modem is available
e) keep a low priority message in a message buffer memory for later transmission if only a cellular modem is accessible
f) choose a cellular modem if both a landline modem having access to a landline network and a cellular modem having access to a cellular network are available but a landline connection is engaged
g) choose a landline modem for messages exceeding a predetermined length or data amount.

9. A patient's device according to claim 1, further comprising a message generator/manager, said message generator/manager is at least indirectly connected to the wireless interface to receive medical or operational data and is adapted to generate a priority indicator to be assigned to a message to be transmitted and to be submitted to the automatic routing/dialling module and/or together with the message to be transmitted.

10. A patient's device according to claim 9, wherein the message generator/manager is at least indirectly connected to the modem selector to enable the modem selector to choose a modem based upon the priority indicator.

11. A patient's device according to claim 9, wherein the message generator/manager is adapted to read data from the incoming data memory and to write message data and assigned priority indicator data into the data buffer memory.

12. A patient's device according to claim 1, further comprising a data buffer memory at least indirectly connected to the automatic routing/dialling module and being adapted to store a message until it is successfully transmitted.

13. A patient's device according to claim 12, additionally comprising a message generator/manager, said message generator/manager is at least indirectly connected to the wireless interface to receive medical or operational data and is adapted to generate a priority indicator to be assigned to a message to be transmitted and to be submitted to the automatic routing/dialling module and/or together with the message to be transmitted, wherein the message generator/manager is adapted to read data from the incoming data memory and to write message data and assigned priority indicator data into the data buffer memory.

14. A patient's device according to claim 1, further comprising an incoming data memory at least indirectly connected to the wireless interface for storing the medical or operational data received via the wireless interface.

15. A patient's device according to claim 14, additionally comprising a message generator/manager, said message generator/manager is at least indirectly connected to the wireless interface to receive medical or operational data and is adapted to generate a priority indicator to be assigned to a message to be transmitted and to be submitted to the automatic routing/dialling module and/or together with the message to be transmitted, wherein the message generator/manager is adapted to read data from the incoming data memory and to write message data and assigned priority indicator data into the data buffer memory.

16. A patient's device comprising:
an at least unidirectional, wireless interface for receiving a data signal, the wireless interface being adapted to receive medical or operational data from an implantable medical device,
a data communication interface for accessing a wide area network or a public telecommunication network or both
wherein the patient's device further comprises an automatic routing/dialling module connected to the data communication interface and being adapted to establish an automatic access to a modem connected to the data communication interface
by automatically selecting one of a plurality of possible connection parameters, the connection parameters to be selected including at least one of
an individual modem, if more than one modem is connected to the data communication interface, and
a prefix number for a remote access to a remote device over a public network
automatically selecting a dial-up telephone number,
wherein the automatic routing/dialling module is adapted to initiate a remote data communication connection via an available modem connected to the data communication interface depending both on the type of available modem and the priority of a message to be communicated, and
additionally comprising a message generator/manager, wherein said message generator/manager is at least indirectly connected to the wireless interface to receive medical or operational data and is adapted to generate a priority indicator to be assigned to a message to be transmitted and to be submitted to the automatic routing/dialling module and/or together with the message to be transmitted.

17. A patient's device of claims 16, wherein the message generator/manager is at least indirectly connected to the modem selector to enable the modem selector to choose a modem based upon the priority indicator.

18. A patient's device according to claim 16, wherein the message generator/manager is adapted to read data from the incoming data memory and to write message data and assigned priority indicator data into the data buffer memory.

19. A patient's device comprising:
an at least unidirectional, wireless interface for receiving a data signal, the wireless interface being adapted to receive medical or operational data from an implantable medical device,
a data communication interface for accessing a wide area network or a public telecommunication network or both
wherein the patient's device further comprises an automatic routing/dialling module connected to the data communication interface and being adapted to establish an automatic access to a modem connected to the data communication interface
by automatically selecting one of a plurality of possible connection parameters, the connection parameters to be selected including at least one of
an individual modem, if more than one modem is connected to the data communication interface, and
a prefix number for a remote access to a remote device over a public network
automatically selecting a dial-up telephone number,
wherein the automatic routing/dialling module is adapted to initiate a remote data communication connection via an available modem connected to the data communication interface depending both on the type of available modem and the priority of a message to be communicated, and
further comprising a data buffer memory at least indirectly connected to the automatic routing/dialling module and being adapted to store a message until it is successfully transmitted.

20. A patient's device according to claim 19, additionally comprising a message generator/manager, said message generator/manager is at least indirectly connected to the wireless interface to receive medical or operational data and is adapted to generate a priority indicator to be assigned to a message to be transmitted and to be submitted to the automatic routing/dialling module and/or together with the message to be transmitted, wherein the message generator/manager is adapted to read data from the incoming data memory and to write message data and assigned priority indicator data into the data buffer memory.

* * * * *